United States Patent [19]

Bryant, III et al.

[11] Patent Number: 4,806,651

[45] Date of Patent: Feb. 21, 1989

[54] PROCESS FOR PREPARING 3,3-DISUBSTITUTED INDOLINES

[75] Inventors: Walter M. Bryant, III, Elkton, Md.; George F. Huhn, New Castle, Del.

[73] Assignee: E. I. Du Pont de Nemours and Company, Wilmington, Del.

[21] Appl. No.: 105,330

[22] Filed: Oct. 7, 1987

[51] Int. Cl.$^4$ ............................................ C07D 401/14
[52] U.S. Cl. .................... 546/256; 544/296; 544/333; 544/357; 544/373
[58] Field of Search ............... 546/256; 544/296, 333, 544/357, 373

[56] References Cited

U.S. PATENT DOCUMENTS 3,574,232 4/1971 Canas - Rodriguez ........ 260/326.11

OTHER PUBLICATIONS

*Ber.*, 46, 3915 (1914).
E. Klingsberg et al., *Pyridines & Its Derivatives*, Pt. II, 191–197 (1961).
J. March, *Advanced Organic Chemistry*, 901–903 (1985).
E. Klingsberg et al., *Pyridine & Its Derivatives*, Pt. II, 203 (1961).
*J. Org. Chem.*, 31, 620 (1966).
*Chem. Rev.*, 85, 129–170 (1985).

*Primary Examiner*—Jane T. Fan

[57] ABSTRACT

Processes for preparing 3,3-disubstituted indolines, particularly 3,3-dipyridine substituted indolines useful to treat cognitive or neurological dysfunction in a mammal, are provided.

10 Claims, No Drawings

PROCESS FOR PREPARING 3,3-DISUBSTITUTED INDOLINES

BACKGROUND OF THE INVENTION

1. Field of the Invention

This invention relates to processes for preparing 3,3-disubstituted indolines and, more particularly, to such processes for preparing 3,3-dipyridine-substituted indolines useful as agents to treat cognitive or neurological dysfunction in a mammal.

2. Background and Prior Art

There is a steadily growing need for effective treatment for Nervous System Disorders causing cognitive and neurological deficiencies. Many of these diseases, of which the incidence generally rises with increasing age, are due to degenerative changes in the nervous system Although in early stages of some diseases certain systems are rather specifically affected (e.g. cholinergic systems in Alzheimer's Disease, and Myasthenia Gravis; the dopaminergic system in Parkinson's Disease, etc.), multiple neurotransmitter system deficiencies (acetylcholine, dopamine, norepinephrine, serotonin) are generally found at later stages of these diseases and are thought to exist at all stages of diseases such as senile dementia, multiinfarct dementia, Huntington's disease, mental retardation, etc. This may explain the generally observed multiple symptomatology which includes cognitive, neurological and effective/psychotic components (see Gottfries, *Psychopharmacol.* 86, 245, 1985). Deficits in the synthesis and release of acetylcholine in the brain are generally thought to be related to cognitive impairment (see Francis et al., *New England J. Med.*, 313, Mar. 7, 1985) whereas neurological deficits (e.g., Parkinsonian Symptoms) and mood/mental changes may be related to impairment of dopaminergic and serotonergic systems, respectively. Other neurological deficits (e.g., Myasthenia Gravis) are related to cholinergic deficiencies in the peripheral nervous system.

Treatment strategies employed hitherto encompass vasoactive drugs like vincamine and pentoxifylline; "metabolic enhancers" like ergoloid mesylates, piracetam and naftidrofuryl; neurotransmitter precursors like 1-DOPA, choline and 5-hydroxytryptamine; transmitter metabolizing enzyme inhibitors like physostigmine; and neuropeptides like adrenocorticotropic hormone and vasopressin-related peptides. Except for 1-DOPA treatment in Parkinson's disease and cholinesterase inhibitor treatment in Myasthenia Gravis, these treatment strategies have generally failed to produce clinically significant improvements (Hollister, *Drugs*, 29, 483, 1985). Another strategy to treat these multiple symptoms is to enhance the residual function of the affected systems by enhancing the stimulus-induced release of neurotransmitters. Theoretically, such an enhancement would improve the signal-to-noise ratio during chemical transmission of information, thereby reducing deficits in processes related to cognition, neurological function and mood regulation.

Compounds which enhance the stimulus-induced release of neurotransmitters, specifically acetylcholine and, in addition, dopamine and serotonin in nervous tissue and improve processes involved in learning and memorization of an active avoidance task are described in coassigned U.S. patent application Ser. No. 944,953, filed Jan. 5, 1987. The process described therein for preparing the 3,3-disubstituted indolines uses expensive picolyl chloride, and undergoes a strong exotherm by the use of aluminum chloride in preparing an intermediate of Formula (I). Thus, there is a need to find a process for preparing these compounds safely in good yield using readily available raw materials.

SUMMARY OF THE INVENTION

According to the present invention there is provided a process for preparing 3,3-disubstituted indolines; more particularly, to a process for preparing a 3,3-disubstituted indoline of the formula:

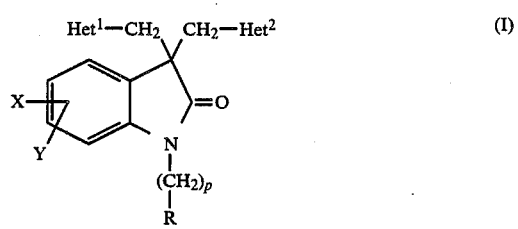

or a pharmaceutically suitable salt thereof wherein:

p is 0 or 1;

R is alkyl of 1–10 carbon atoms, cycloalkyl or 3–8 carbon atoms, 2-, 3- or 4-pyridyl, or

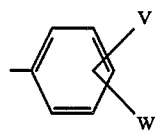

V, W, X and Y independently are H, halo, alkyl of 1–3 carbon atoms, $OR^1$, $NO_2$, $CF_3$, CN or $NR^1R^2$;

$R^1$ and $R^2$ independently are H or alkyl of 1–3 carbon atoms;

$Het^1$ and $Het^2$ independently are 2- or 4-pyridyl, 2-, 4- or 6-pyrimidinyl, or 2-pyrazinyl, optionally substituted with an alkyl group of 1–3 carbon atoms, which comprises:

(1) contacting at a temperature of at least 100° C. a compound of Formula (II) in a solution with at least one equivalent weight of $Het^1$—$CH_3$, said compound of Formula (II) having the formula:

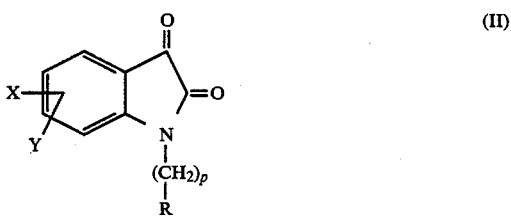

where X, Y, p and R are defined above, for a time sufficient to obtain a compound of the formula:

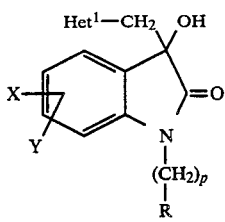

(2) dehydrating the compound of Formula (III) prepared in step (1) to obtain a compound of the formula:

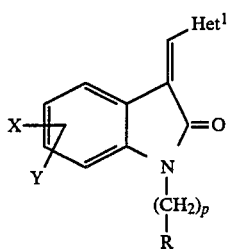

(3) reducing the compound of Formula (IV) in solution with a boron hydride or by catalytic hydrogenation under conditions such that there is no reduction of C=O or of a double bond in $Het^1$, to obtain a compound of the formula:

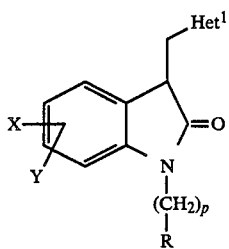

and (4) contacting the compound of Formula (V) obtained in step (4), or a salt formed therefrom, in a basic solution with a compound of the formula

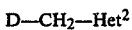

where $Het^2$ is defined above, and
D is a displaceable group.

PREFERRED CONDITIONS

Step (1)—Acetic acid is the preferred solvent. Temperature is preferably in the range of 100°–150° C., most preferably in the range of 120°–130° C. Other solvents and reaction conditions for carrying out Step (1) will be described.

Step (2)—Dehydration preferably is carried out with an acid anhydride (acetic anhydride preferred) at a temperature in the range of about 50°–150° C., preferably about 100°–130° C. Other dehydration conditions will be described.

Step (3)—Sodium borohydride in methanol is the preferred reducing agent. Other useful reducing agents and conditions will be described.

Step (4)—Aqueous sodium hydroxide is the preferred base in the basic solution. Preferred and other solvents, and reaction conditions will be described. D preferably is halogen, methanesulfonate or p-toluene sulfonate.

Preferred compounds of Formula (I) are those where:
p is 0;
X and Y are H;
R is $CH_3$, phenyl or m-chlorophenyl; or —$Het^1$ and $Het^2$ are each 4-pyridyl.

SYNTHESIS

Compounds of the Formula (I) (Scheme I) are prepared by reaction of a substituted isatin (II) with $Het^1$—$CH_3$, e.g., an alkyl pyridine, such as 4-picoline, in acetic acid at 120°–130° C. to yield the aldol addition product (III). The reaction can also be carried out in 4-picoline itself as solvent. The product can be isolated via dilution with methylene chloride followed by filtration and recrystallization of the product. Other high boiling solvents such as hydrocarbons (xylenes or toluene) containing an excess of 4-picoline can also be used for this reaction. Substituted isatins (II) are well described in the literature. 1-Phenyl isatin is prepared from diphenylamine and oxalyl chloride as described in *Ber.*, 46, 3915 (1914). Condensation of alkyl pyridines with carbonyl compounds is described in E. Klingsberg, et al., *Pyridines and Its Derivatives*, Pt. II, 191–197 (1961).

Dehydration of (III) to produce (IV) preferably is carried out neat with acetic anhydride at a temperature between 100°–130° C. This reaction can also be performed in the presence of acetic acid and other aprotic solvents such as toluene or xylene. Useful temperatures range from 50°–150° C. Other methods of dehydration familiar to one skilled in the art include the use of zinc chloride, other acid anhydrides, phosphorus pentoxide, potassium bisulfate, and sulfuric acid as described in J. March, *Advanced Organic Chemistry*, 901–903, (1985). Dehydration of carbinols (III) resulting from the condensation of alkyl pyridines with carbonyl compounds is described in E. Klingsberg, et al., *Pyridine and Its Derivatives*, Pt. II, 203 (1961).

Compounds of Formula (IV) are preferably isolated prior to further processing for characterization. Isolation can be carried out by any of the well-known isolation procedures known in the art. For example, the compounds can be filtered, solvents evaporated, etc.

Compounds of the Formula (V) are obtained via reduction of the compounds of (IV). Treatment of (IV) with sodium borohydride in methanol is the preferred method for conversion of (IV) to (V). This method is illustrated in *J. Org. Chem.*, 31, 620 (1966). (V) may also be obtained via transfer hydrogenation as described in *Chem. Rev.*, 85, 129–170 (1985) or via catalytic hydrogenation in acetic acid or ethyl acetate under standard conditions known to one skilled in the art. Use of these reducing reactions will not reduce the C=O or a double bond in $Het^1$. Preferred temperatures range from about 25°–80° C. The preferred pressure for catalytic hydrogenation is 1 atm of hydrogen.

The conversion of (V) to (I) is preferably performed in a methanol-water mixture using sodium hydroxide as the preferred base, followed by the reaction of the resultant anionic species with a compound of the of the resultant anionic species with a compound of the formula D—$CH_2$—$Het^2$ where D is preferably halogen, methanesulfonate or p-toluenesulfonate. Other alcohols such as ethanol, isopropanol, n-propanol can be substituted for methanol. Other bases such as potassium hydroxide, lithium hydroxide, and quaternary amines such as N-benzyltrimethyl ammonium hydroxide are also acceptable. Preparation of (I) from (V) can also be accomplished under phase-transfer catalysis using toluene-50% sodium hydroxide as the solvents and hexadecyltributyl phosphonium bromide as the catalyst.

The compounds of this invention and their preparation can be understood further by the following examples in which all temperatures are in degrees Celsius and parts and percentages are by weight unless otherwise indicated.

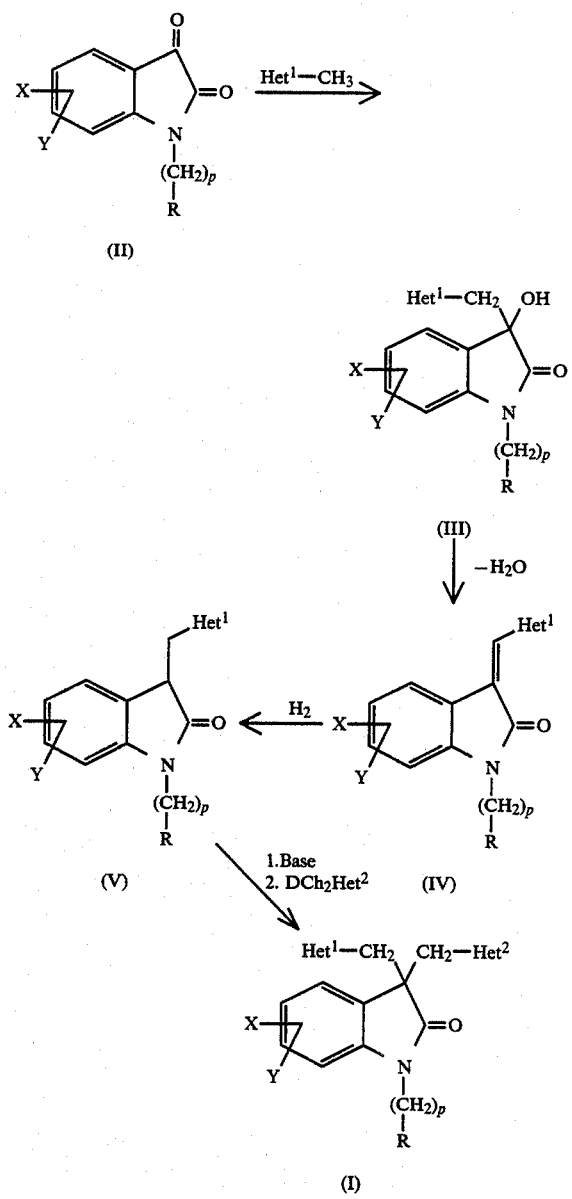

EXAMPLE 1

Part A:
3-(4-Pyridinylmethylidene)-1-phenylindolin-2-one

A solution of oxalyl chloride (175 mL, 254.6 g, 2.01M) was cooled to 5°, and a solution of diphenylamine (320 g, 1.89M) in toluene (580 mL) added over 8 minutes. The mixture was heated to 50°-65° for 74 minutes. The mixture was then heated to 125° to distill toluene and excess oxalyl chloride; total distillate collected was 630 mL. The solution was then refluxed at 125°±2° for 20 hours to form indoline-2,3-dione. The mixture was cooled to 104°, and a solution of 4-picoline (215 mL, 205.7 g, 2.21M) in acetic acid (750 mL) was added over 17 minutes. The mixture was heated to 130° to remove excess toluene via acetic acid/toluene azeotrope. Additional acetic acid (750 mL) was added during the distillation. A total of 875 mL distillate containing 260 mL toluene was collected. The mixture was cooled to 115°, and acetic anhydride (360 mL, 389.5 g, 3.81M) added over 10 minutes while heating to 120°-130°. The mixture was stirred at 120°±2° for 1.75 hours, and then cooled to 76°. Water (530 mL) was added over 7 minutes followed by isopropanol (430 mL) while maintaining the temperature between 82° and 63°. The mixture was cooled to ambient temperature overnight, then to 0°-5°. The crude product was collected by filtration, washed with isopropanol (2.16 l) and water 1.64 l). Drying in a vacuum oven at 80°-90° yielded the title compound (422.6 g, 75%) as an orange crystalline solid. M.P.: 160.1°-161.9°.

Part B:
3,3-bis(4-pyridinylmethyl)-1-phenylindolin-2-one

A slurry of 3-(4-pyridinylmethylidene)-1-phenylindolin-2-one (80 g, 0.268M) in methanol (600 mL) was cooled to 6°. Sodium borohydride pellets (0.2 g each, 3.19 g total 0.084M) were added over 20 minutes with gentle cooling. The mixture was stirred for 50 minutes, cooled to 7°, and 10N sodium hydroxide (64 mL, 0.64M) added over 11 minutes. A solution of 4-picolychloride hydrochloride (4.85 g, 0.296M) in water (160 mL) was then added over 28 minutes while maintaining a temperature of 10°-15°. Cooling was then removed, and 10N sodium hydroxide (80 mL, 0.8M) added over 10 minutes. The mixture was stirred for 2 hours and then water (580 mL) added over 45 minutes. The slurry was cooled to 10°-15°, stirred for 10 minutes, and the solids collected by filtration. The solids were then reslurried in water (450 mL), filtered, and washed with water. Drying in a vacuum oven at 85°-95° yielded 89.4 g (85%) crude title compound. This crude product (85 g) was recrystallized in isopropanol and water to yield 77.3 g of the title compound (90% recovery). M.P.: =186°-188°.

EXAMPLE 2

3-(4-Pyridinylmethyl)-1-phenylindolin-2-one Hydrochloride

A mixture of 3-(4-pyridinylmethylidene)-1-phenylindolin-2-one (1211 g, 4.06M), formic acid (260 mL, 317 g, 6.89M), isopropanol (6.5 l), and 5% palladium on carbon catalyst (180 g) was heated to 70°. Additional formic acid (1000 mL, 1220 g, 26.50M) was added over 125 minutes while heating to 82°. The mixture was heated at reflux for 70 minutes and cooled to 75°. The catalyst was removed by filtration and washed with isopropanol (300 mL). The solution was heated to 51°, and concentrated hydrochloric acid (530 mL, 6.4M) added over 75 minutes. The resulting slurry was cooled to 15°, the title compound isolated by filtration, and washed with isopropanol (2 l). The solids were then reslurried in isopropanol (3.5 l), filtered, and dried in a warm vacuum oven. The title compound yield was 1126 g (82%) of tan crystalline solid. M.P.: 244°–248° (Dec.). % Chloride: 10.64% (Theory: 10.5%). % H₂O: 0.06%.

The compounds of Examples 1 and 2 above, as well as the compounds which were prepared or could be prepared using the procedures of the aforementioned examples, are shown in Table I.

TABLE 1

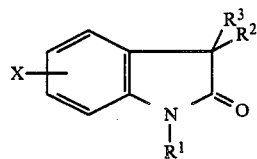

| Ex. | X | R¹ | R² | R³ | m.p. °C. |
|---|---|---|---|---|---|
| 1 | H | Ph | CH₂-(4-pyridyl) | CH₂-(4-pyridyl) | 186–188 |
| 2 | H | Ph | CH₂-(4-pyridyl) | H | 244–248 (HCl salt) |
| 3 | H | Ph | CH₂-(4-pyridyl) | OH | |
| 4 | H | Ph | CH₂-(2-pyridyl) | OH | |
| 5 | H | Ph | CH₃ | OH | |
| | | | CH₂-(4-pyridyl) | | |
| 6 | H | Ph | CH₂-(pyrimidinyl) | OH | |
| 7 | H | H | CH₂-(4-pyridyl) | OH | |
| 8 | H | H | CH₂-(3-pyridyl) | CH₂-(4-pyridyl) | |
| 9 | 5-F | H | CH₂-(4-pyridyl) | OH | |
| 10 | 4-Cl | H | CH₂-(4-pyridyl) | OH | |

TABLE 1-continued

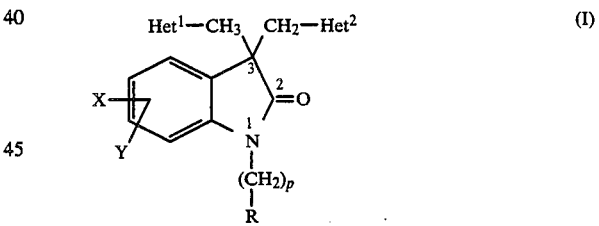

| Ex. | X | R¹ | R² | R³ | m.p. °C. |
|---|---|---|---|---|---|
| 11 | 6-Cl | H | CH₂-(4-pyridyl) | OH | |
| 12 | H | Ph | CH₂-(4-pyridyl) | CH₂-(3-pyridyl) | |
| 13 | H | Ph | CH₂-(4-pyridyl) | CH₂-(2-pyridyl) | |
| 14 | H | Ph | CH₂-(4-pyridyl) | CH₂-Ph | |
| 22 | H | Ph | CH₂-(pyrimidinyl) | CH₂-(pyrazinyl) | |

What is claimed is:

1. A process for preparing a 3,3-disubstituted indoline of the formula:

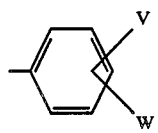

or a pharmaceutically suitable salt thereof wherein:
p is 0 or 1;
R is alkyl of 1–10 carbon atoms, cycloalkyl or 3–8 carbon atoms, 2-, 3- or 4-pyridyl, or

[phenyl with V and W substituents]

V, W, X and Y independently are H, halo, alkyl of 1–3 carbon atoms, OR¹, NO₂, CF₃, CN or NR¹R²;
R¹ and R² independently are H or alkyl of 1–3 carbon atoms;
Het¹ and Het² independently are 2- or 4-pyridyl, 2-, 4- or 6-pyrimidinyl, or 2-pyrazinyl, optionally substituted with an alkyl group of 1–3 carbon atoms, which comprises:

(1) contacting at a temperature of between 100° and 150° C. compound of Formula (II) in a solution with at least one equivalent weight of Het¹—CH₃, said compound of Formula (II) having the formula:

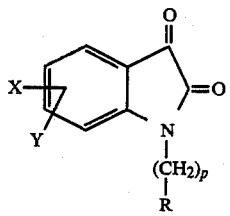 (II)

where X, Y, p and R are defined above, for a time sufficient to obtain a compound of the formula:

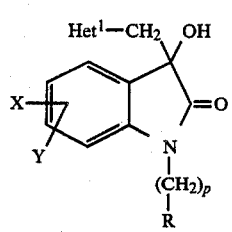 (III)

(2) dehydrating the compound of Formula (III) prepared in step (1) to obtain a compound of the formula:

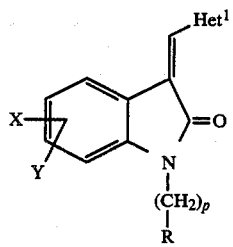 (IV)

(3) reducing the compound of Formula (IV) in solution with a boron hydride or by catalytic hydrogenation under conditions such that there is no reduction of C=O or of a double bond in Het¹, to obtain a compound of the formula:

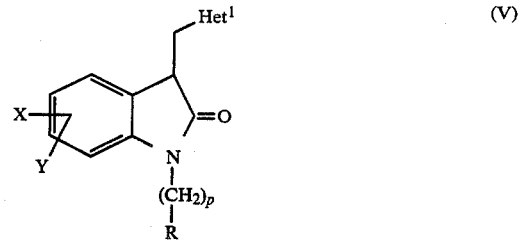 (V)

and (4) contacting the compound of Formula (V) obtained in step (4), or a salt formed therefrom, in a basic solution with a compound of the formula

D—CH₂—Het² where Het² is defined above, and
D is a nucleophilic displaceable group.

2. The process of claim 1 wherein p is O, X and Y are H, R is CH₃, phenyl or m-chlorophenyl.

3. The process of claim 2 wherin Het¹ and Het² are each 4-pyridyl.

4. The process of claim 3 wherein step (1) is conducted in acetic acid at a temperature in the range of about 100°–150° C.

5. The process of claim 3 wherein step (2) is conducted in an acid anhydride at a temperature in the range of about 50°–150° C.

6. The process of claim 3 wherein in step (3) the compound of Formula (IV) is contacted with sodium borohydride in methanol.

7. The process of claim 3 wherein in step (4) the basic solution is aqueous sodium hydroxide and D is halogen, methanesulfonate or p-toluenesulfonate.

8. The process of claim 1 wherein the compound of Formula (IV) is isolated prior to being reduced.

9. The process of claim 3 wherein:
(a) step (1) is conducted in acetic acid at a temperature in the range of about 120°–130° C.;
(b) step (2) is conducted in acetic anhydride at a temperature in the range of about 100°–130° C.;
(c) in step (3) sodium borohydride in methanol is the reducing agent; and
(d) in step (4) the basic solution is aqueous sodium hydroxide and D is halogen, methanesulfonate or p-toluenesulfonate.

10. The process of claim 9 wherein the compound of Formula (IV) is isolated prior to being reduced.

* * * * *